United States Patent [19]

Shimamura et al.

[11] 4,432,959
[45] Feb. 21, 1984

[54] PROCESS OF PRODUCING SODIUM CYANUARATE

[75] Inventors: Tadao Shimamura; Naoki Kano, both of Tokushima, Japan

[73] Assignee: Shikoku Chemicals Corporation, Kagawa, Japan

[21] Appl. No.: 404,867

[22] Filed: Aug. 3, 1982

[51] Int. Cl.$^3$ .............................................. C01C 3/00
[52] U.S. Cl. ............................................... 423/365
[58] Field of Search ......................................... 423/365

[56] References Cited
FOREIGN PATENT DOCUMENTS 1006489 10/1965 United Kingdom ................ 423/365
1216063 12/1970 United Kingdom ................ 423/365

*Primary Examiner*—Edward J. Meros
*Assistant Examiner*—Wayne A. Langel

[57] ABSTRACT

A process for producing sodium cyanurate in the powdery form is disclosed. In this method, iso cyanuric acid is reacted with sodium carbonate or sodium hydrogencarbonate or a mixture of sodium carbonate and sodium hydrogencarbonate by mixing the raw materials in powdery form and in the presence of water in a range, in which hydrates can be formed from the raw materials at room temperature, while holding the system at a temperature at which free water can be produced.

5 Claims, No Drawings

PROCESS OF PRODUCING SODIUM CYANUARATE

BACKGROUND OF THE INVENTION

1. Field of the Invention

This invention relates to a process of producing sodium cyanurate and, more particularly, to a process of producing sodium cyanurate which is suited for carrying it out on an industrial scale.

2. Description of the Prior Art

Sodium cyanurate is a compound attracting attentions as an active chlorine stabilizer in pool water.

It is well known in the art that sodium cyanurate is prepared on an industrial scale by neutralizing iso cyanuric acid by adding an alkali such as caustic soda or sodium carbonate in the presence of water. This process, however, requires a great quantity of water for dissolving iso cyanuric acid for the solubility thereof with respect to water at room temperature is very low, namely less than 1%. Therefore, the apparatus employed inevitably has a large size. In addition, the separation and recovery of the reaction products requires a complicated process, giving rise to various problems in practice, for instance in connection with the draining of water. For these reasons, the method has not yet been an industrially established method.

OBJECTS AND SUMMARY OF THE INVENTION

Accordingly, it is an object of the present invention to provide an improved process of producing sodium cyanurate, which can avoid the above-described disadvantages and difficulties of the prior art.

More particularly, it is an object of this invention to provide a process of producing sodium cyanurate in the form of dry powder.

The inventors have conducted extensive researches and investigations in the light of the above affairs, and the invention is predicated on a finding that sodium cyanurate can be obtained by reacting iso cyanuric acid in powder form with sodium carbonate or sodium hydrogencarbonate in powder form, or with a mixture thereof, wherein at least one of said starting materials in powder form is a hydrate, or both of said starting materials are anhydrates, in which case water is added to the anhydrates in an amount sufficient to produce a hydrate at room temperature, and wherein the starting materials are mixed and kneaded together in powder form while the materials are maintained at a temperature at which water may be liberated from said hydrate.

The above, and other objects, features and advantages of the present invention, will be readily apparent from the following detailed description of the invention.

DETAILED DESCRIPTION OF PREFERRED EMBODIMENTS

In the process according to the invention, iso cyanuric acid is charged as a hydrate into a reaction vessel, or iso cyanuric acid is reacted with water present in a reaction system to produce the hydrate. Thus, the material can be mixed with sodium carbonate or sodium hydrogencarbonate very uniformly. The reaction system is then heated to a temperature above approximately 58° C., at which a transition of the iso cyanuric acid hydrate takes place. As a result, free water is produced. Alkali is dissolved in the liberated water. The neutralizing reaction thus brought about further produces water. The water produced as a result of the neutralization causes a further reaction. Since the reaction takes place in a fashion of chain reactions, water in the reaction system is gasificated by $CO_2$ gas produced in the reaction of iso cyanuric acid with sodium carbonate or sodium hydrogencarbonate. Thus, the reaction system in the reaction vessel can be mixed while substantially maintaining the system as dry powder. The intended product thus can be obtained under quantitative control. In addition, any drying step usually can be dispensed with.

In practicing the present invention, less than about 50 percent of water related to iso cyanuric acid may be present in the reaction system for uniformly kneading the reaction system in the powder form, because both iso cyanuric acid and sodium carbonate can form hydrates—for instance, iso cyanuric acid can form dihydrate while sodium carbonate can form heptahydrate or decahydrate. In this case, hydrates of iso cyanuric acid or sodium carbonate may be used as starting materials. Alternatively, anhydrous cyanuric acid and anhydrous sodium carbonate or sodium hydrogencarbonate or a mixture of anhydrous sodium carbonate and sodium hydrogencarbonate may be used as starting material, provided that water is added to these materials in an amount sufficient to produce a hydrate at room temperature, the resulting mixture being kneaded to yield a hydrate. For proceeding the reaction, the reaction mixture needs to be heated to a temperature at which water can be liberated from the hydrate (transition temperature). Since the transition temperature for iso cyanuric acid dihydrate is 57° C. while that for sodium carbonate decahydrate and that for sodium carbonate heptahydrate are 32° to 35° C. and 35° C., respectively, the reaction mixture is heated to 60° to 100° C. and preferably to 60° to 80° C.

Sodium cyanurate that is obtained by the process according to the invention has rich fluidity and is free from any cakes. Thus, it can be used in the form of powder and has a very high solution velocity with respect to water.

The invention will be understood more readily by reference to the following examples; however, these examples are intended to illustrate the invention and are not to be construed to limit the scope of the invention.

EXAMPLE 1

100 Kg of iso cyanuric acid hydrate with a water content of 16.5% was charged into a 200 l ribbon blender provided with a heating jacket, and then 34 Kg of an hydrous sodium carbonate was charged while agitating the system at a speed of 50 rpm.

The reaction was caused to proceed gradually, and the temperature is increased from 28° C. to 42° C. At this stage, however, the reaction was not completed. The system was continually mixed for further two hours with the temperature of the reaction system elevated to 60° to 70° C. by passing steam through the jacket. As a result, 111.4 Kg of sodium cyanurate in the form of dry powder having rich fluidity could be obtained.

1.8% of water was liberated, and no subsequent drying was needed.

An infrared spectral analysis of the product revealed that the product was monosodium cyanurate monohydrate.

EXAMPLE 2

83.5 Kg of dry iso cyanuric acid and 54.3 Kg of sodium hydrogencarbonate were charged into the same device as in Example 1, and 12 Kg of water added while mixing the system. Subsequently, the system was continually mixed for further 150 minutes with the temperature of the system elevated to 75° C. As a result, 115.6 Kg of sodium cyanurate could be obtained.

An infrared spectral analysis of the product revealed that the product was monosodium cyanurate monohydrate. Approximately 3% of free water was recognized, but the product had rich fluidity and no caking was recognized.

EXAMPLE 3

83.0 Kg of dry iso cyanuric acid, 34 Kg of anhydrous sodium carbonate and 74.6 Kg of sodium carbonate heptahydrate were charged into the same device as in Example 1 and mixed together. Subsequently, the reaction was continued for 3 hours with the system held at 100° C., and 125 Kg of sodium cyanurate could be obtained.

An infrared spectral analysis proved that the product was disodium cyanurate monohydrate containing 1.7% of free water.

We claim:

1. A process of producing sodium isocyanurate by reacting iso cyanuric acid in powder form with a carbonate in powder form selected from the group consisting of sodium carbonate, sodium hydrogencarbonate, and mixtures thereof, wherein at least one of said starting materials in powder form is a hydrate, comprising mixing the starting materials together while maintaining the same at a temperature at which free water is liberated from said hydrate.

2. The process according to claim 1, wherein isocyanuric acid hydrate and anhydrous sodium carbonate are used as starting materials and free water is liberated from said iso cyanuric acid hydrate.

3. The process according to claim 1, wherein anhydrous isocyanuric acid and sodium carbonate hydrate are used as starting materials and free water is liberated from said sodium carbonate hydrate.

4. The process according to claim 1 wherein a temperature ranging from 60° to 80° C. is employed.

5. A process of producing sodium isocyanurate by reacting isocyanuric acid in powder form with a carbonate in powder form selected from the group consisting of sodium carbonate, sodium hydrogen carbonate and mixture thereof, wherein each of said starting materials are in the anhydrated state, comprising adding water to the anhydrates in an amount sufficient to produce hydrates thereof at room temperature, and mixing the same together at a temperature and for a time sufficient to liberate free water from said hydrates.

* * * * *